United States Patent [19]

Choksi

[11] Patent Number: 5,727,594
[45] Date of Patent: Mar. 17, 1998

[54] LOW ACTUATION PRESSURE UNIDIRECTIONAL FLOW VALVE

[76] Inventor: Pradip Choksi, 9614 Cozycroft, Suite F, Chatsworth, Calif. 91311

[21] Appl. No.: 385,810

[22] Filed: Feb. 9, 1995

[51] Int. Cl.$^6$ .................................................. F16K 15/14
[52] U.S. Cl. .......................... 137/859; 137/537; 137/559; 604/247
[58] Field of Search .................................. 137/496, 859, 137/535, 537, 559; 604/247

[56] References Cited

U.S. PATENT DOCUMENTS

| | | | |
|---|---|---|---|
| 2,249,971 | 7/1941 | Mecorney | 137/537 |
| 3,063,461 | 11/1962 | Rudolph | 137/537 X |
| 3,845,786 | 11/1974 | Papst et al. | 137/535 |
| 4,045,009 | 8/1977 | Pees | 137/859 X |
| 4,210,173 | 7/1980 | Choksi et al. | 137/512.3 |
| 4,244,379 | 1/1981 | Smith | 604/247 X |
| 4,566,493 | 1/1986 | Edwards et al. | 604/247 X |
| 4,712,583 | 12/1987 | Pelmulder et al. | 137/859 X |

OTHER PUBLICATIONS

Plast–O–Matic Valves, Inc., "self–Closing Diaphragm Check Valves", Catalog CKM–2, Dec. 1993, 2 pgs.
Burron OEM Division, "Quality Check Valves from Burron", 1 pg., 1994 (No Month).

MEDLIT, "High Flow Back Check Valve" form Burron, Nov. 1994, 1 pg.
"Vernay V–Ball" Valve, 1 pg., Date Unknown.
"Umbrella Check" Valve, 1 pg., Date Unknown.
"Duckbill" Valve, 1 pg., Date Unknown.

*Primary Examiner*—John Rivell
*Attorney, Agent, or Firm*—Stetina Brunda; Garred & Brucker

[57] ABSTRACT

A low actuation pressure, unidirectional flow valve comprising a housing including a fluid flow passage extending therethrough which defines first and second sections. Disposed within the housing between the first and second sections is a valve member. The valve member comprises an annular ring portion having a disc portion disposed therewithin. Extending between the ring and disc portions are at least two spirally shaped connecting arm portions. The ring, disc and connecting arm portions define at least two side openings. The valve member is movable between a closed position wherein the disc portion covers and seals the first section of the flow passage, and an open position wherein the disc portion is separated from the first section and fluid flows from the first section to the second section via the side openings.

23 Claims, 2 Drawing Sheets

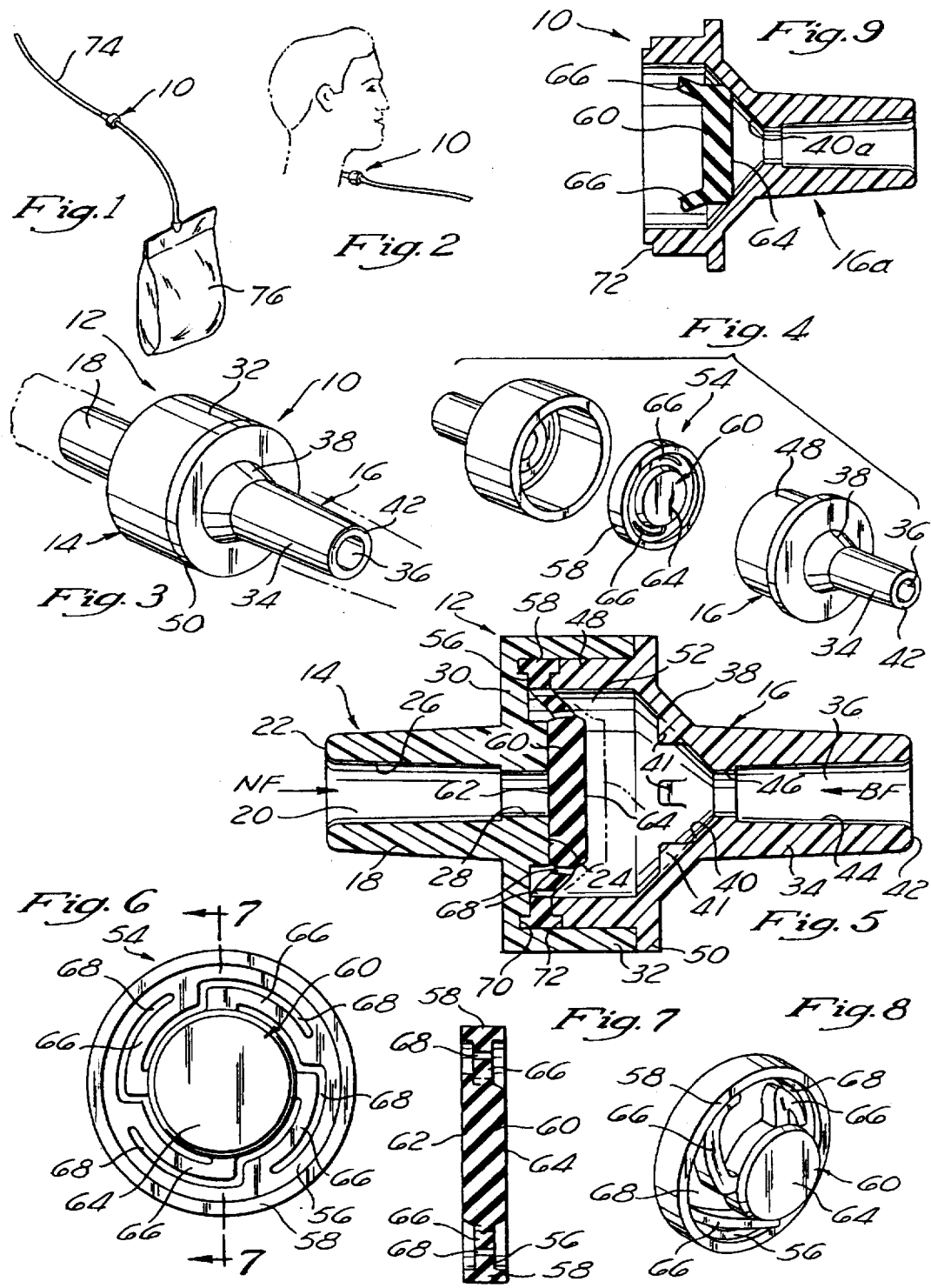

LOW ACTUATION PRESSURE UNIDIRECTIONAL FLOW VALVE

FIELD OF THE INVENTION

The present invention relates generally to check valves, and more particularly to a unidirectional flow valve which is adapted to open under low pressure and provide a high flow rate with no retrograde leakage.

BACKGROUND OF THE INVENTION

In medical fluid handling applications, it is often necessary to maintain flow in a single direction while preventing any retrograde or back flow. In this respect, when blood is drained from a patient's wound site or urine drained from a patient's bladder into a fluid drainage or collection bag via a drainage line, it is important to prevent such fluids from flowing back into the patient. Such back flow is typically prevented through the placement of a one-way check valve within the drainage line. As will be recognized, the check valve used in these types of applications must have a very low opening pressure. Indeed, if the opening pressure of the check valve is high, the fluid will not flow therethrough, but rather accumulate upstream of the check valve thereby possibly resulting in medical complications.

In addition to the check valve needing to have a low opening pressure, it must also provide very low flow resistance in order to maintain a continuous flow of the fluid at low pressures. The check valve also must not leak in the reverse direction when the back pressure to which it is subjected is very small. As will be recognized, such back flow or retrograde leakage could occur if the collection bag is elevated slightly above the patient's drainage site. It is also important that the check valve function properly regardless of its horizontal or vertical orientation.

In the prior art, check valves of several different designs are typically incorporated into the drainage line used in relation to the above described medical applications. The most commonly used check valves are the duck-bill and disc or umbrella designs, both of which are inexpensive to manufacture but do not perform satisfactorily under all conditions. In this respect, the duck-bill valves tend to leak under low back pressure, with the disc valves generally providing high resistance to flow and being susceptible to clogging. With particular respect to urine drainage applications, some urine drainage or collection bags incorporate a flapper valve as an alternative to a duck-bill or disc valve for purposes of providing a large opening for unimpeded flow. Though the flapper valve is simple in design, it is also deficient in that it tends to leak under low back pressure or when not properly oriented. The present invention is intended to overcome these and other deficiencies associated with prior art check valves by providing a unidirectional flow valve which has a low actuation or opening pressure and provides a high flow rate with no retrograde leakage.

SUMMARY OF THE INVENTION

In accordance with the present, invention there is provided a low actuation pressure, unidirectional flow valve comprising a housing which includes a fluid flow passage extending therethrough. In the preferred embodiment, the housing itself comprises a first housing half which defines a first section of the flow passage and a second housing half which defines a second section of the flow passage. Formed within the first housing half is an annular shoulder which defines one end of the first section of the flow passage, while formed within the second housing half are a plurality of bosses. The second housing half is partially inserted into and rigidly attached to the first housing half. Both the first and second housing halves are preferably fabricated from a plastic material.

Disposed within the housing between the first and second sections of the flow passage is a valve member. The valve member preferably comprises an annular ring portion and a disc portion which is disposed within the ring portion. Extending between the ring and disc portions are at least two connecting arm portions. The ring, disc and connecting arm portions define at least two side openings. The valve member is moveable between a closed position wherein the disc portion covers and seals the first section of the flow passage and an open position wherein the disc portion is separated from the first section and fluid flows from the first section to the second section via the side openings. In particular, the disc portion is abutted and sealed against the shoulder of the first housing half when the valve member is in the closed position, and separated from the shoulder when the valve member is in the open position.

In the preferred embodiment, each of the connecting arm portions is spirally shaped, with the valve member being formed such that the movement thereof between the closed and open positions is facilitated solely by the flexion of the connecting arm portions. Due to the connecting arm portions being spirally shaped, each of the side openings of the valve member has a serpentine configuration. The valve member preferably includes four (4) connecting arm portions which are symmetrically positioned between the ring and disc portions, and four (4) side openings which are defined by the ring, disc and connecting arm portions.

To prevent any undesirable distortion of the disc portion when the valve member is in the closed position, the disc portion is preferably formed having a thickness which is approximately twice the thickness of the connecting arm portions. Additionally, to provide low flow resistance, the cross-sectional area of the side openings exceeds the cross-sectional area of the first section of the flow passage, even when the valve member is in the closed position. The movement of the valve member from the closed to the open positions solely by the flexion (rather than the stretching) of the connecting arm portions provides the valve with a low opening pressure. The valve member is preferably fabricated from an elastomeric material. Alternatively, the disc portion may be fabricated from a rigid or semi-rigid material, with only the ring and connecting arm portions being fabricated from an elastomeric material.

BRIEF DESCRIPTION OF THE DRAWINGS

These, as well as other features of the present invention, will become more apparent upon reference to the drawings wherein:

FIG. 1 is a perspective view of the valve of the present invention as incorporated into the drainage line of a collection bag;

FIG. 2 is a perspective view of the valve of the present invention as attached to a tracheotomy tube of a patient;

FIG. 3 is a perspective view of the valve of the present invention;

FIG. 4 is an exploded view of the valve shown in FIG. 3;

FIG. 5 is a cross-sectional view of the valve of the present invention;

FIG. 6 is a front elevational view of a valve member of the valve;

FIG. 7 is a cross-sectional view of the valve member taken along line 7—7 of FIG. 6;

FIG. 8 is a perspective view of the valve member in its operative orientation as shown in FIG. 5;

FIG. 9 is a cross-sectional view of a second half of the housing of the valve which is constructed in accordance with a second embodiment of the present invention;

DETAILED DESCRIPTION OF THE PREFERRED EMBODIMENTS

Figure 10A:
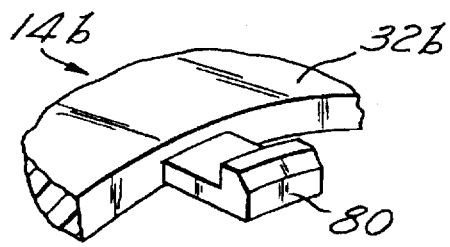
FIG. 10a is a partial perspective view of a first half of the housing of the valve which is constructed in accordance with a second embodiment of the present invention.

Referring now to the drawings wherein the showings are for purposes of illustrating preferred embodiments of the present invention only, and not for purposes for limiting the same, FIG. 3 perspectively illustrates a unidirectional flow valve 10 constructed in accordance with the preferred embodiment of the present invention. As will be discussed in more detail below, the valve 10 is adapted to have a low actuation or opening pressure, and provide a high flow rate at low pressure with very low flow resistance or restriction and no retrograde leakage. The valve 10 may be used for all fluids, i.e., both gases and liquids.

Referring now to FIGS. 3-5, the valve 10 comprises a housing 12 which includes a fluid flow passage extending therethrough. The housing 12 itself comprises a first housing half 14 and a second housing half 16. The first housing half 14 includes an elongate, tubular adapter portion 18 having an orifice 20 extending therethrough which defines a first section of the flow passage. The adapter portion 18 includes a rounded outer end 22 which defines one open end of the orifice 20, and an inner, annular shoulder 24 which defines the other open end of the orifice 20. As seen in FIG. 5, a first region of the orifice 20 extending to the outer end 22 is defined by a first inner surface portion 26 of the adapter portion 18 which has a tapered configuration. A second region of the orifice 20 extending to the shoulder 24 is defined by a second inner surface portion 28 of the adapter portion 18 which is of constant diameter. In addition to the adapter portion 18, the first housing half 14 includes a base portion 30 which extends radially from the adapter portion 18 in close proximity to the shoulder 24 thereof. Extending perpendicularly from the periphery of the base portion 30 away from the outer end 22 is an annular sleeve portion 32.

The second housing half 16 of the housing 12 is configured similarly to the first housing half 14, and includes an elongate, tubular adapter portion 34 having an orifice 36 extending therethrough which defines a second section of the flow passage. The adapter portion 34 of the second housing half 16 transitions into a flared portion 38 which defines a beveled, frusto-conical inner surface 40. Formed on the inner surface 40 of the flared portion 38 are four (4) equidistantly spaced bosses 41, the use of which will be discussed in more detail below. As further seen in FIG. 5, one open end of the orifice 36 is defined by the rounded outer end 42 of the adapter portion 34, with the other open end being defined by the inner surface 40 of the flared portion 38. Like the orifice 20 previously described, a first region of the orifice 36 extending to the outer end 42 is defined by a first inner surface portion 44 of the adapter portion 34 which has a tapered configuration. A second region of the orifice 36 extending to the inner surface 40 is defined by a second inner surface portion 46 of the adapter portion 34 which is of constant diameter. The diameter of the second region of the orifice 36 is substantially equal to the diameter of the second region of the orifice 20. The flared portion 38 of the second housing half 16 itself transitions into an annular wall portion 48. Extending radially outward from the end of the wall portion 48 adjacent the flared portion 38 is a continuous flange portion 50.

In the valve 10, the second housing half 16 is partially inserted into and rigidly attached to the first housing half 14. In particular, the wall portion 48 of the second housing half 16 is slidably inserted into the sleeve portion 32 of the first housing half 14, the inner diameter of which slightly exceeds the outer diameter of the wall portion 48. The insertion of the wall portion 48 into the sleeve portion 32 is limited by the abutment of the flange portion 50 against the rim of the sleeve portion 32. Subsequent to the full insertion of the wall portion 48 into the sleeve portion 32, the flange portion 50 is ultrasonically joined to the rim of the sleeve portion 32, thus rigidly attaching the first and second housing halves 14, 16 to each other. Though preferably being attached to each other via an ultrasonic welding process, the first and second housing halves 14, 16, may also be attached to each other via an adhesive or solvent. The first and second housing halves 14, 16 are preferably fabricated from a transparent plastic material, though other materials may be utilized as an alternative. When attached to each other, the first and second housing halves 14, 16 define an interior chamber 52 which is positioned between and communicates with the orifices 20, 36.

Referring now to FIGS. 4-8, the valve 10 constructed in accordance with the present invention further comprises a valve member 54 which is disposed within the housing 12, and in particular the interior chamber 52 thereof. In the preferred embodiment, the valve member 54 is integrally molded from an elastomeric material and comprises an outer, annular ring portion 56. The ring portion 56 itself includes a perpendicularly extending flange portion 58 which defines the peripheral edge thereof. Disposed within the ring portion 56 is a circularly configured disc portion 60 which defines a generally planar inner surface 62 and a generally planar outer surface 64. Extending between the ring portion 56 and disc portion 60 are four (4) spirally shaped connecting arm portions 66. The connecting arm portions 66 are symmetrically positioned between the ring and disc portions 56, 60. As best seen in FIG. 6, the ring, disc and connecting arm portions 56, 60, 66 define four (4) side openings 68, each of which has a serpentine configuration. The combined cross-sectional area of the side openings 68 exceeds the cross-sectional area of each of the second regions of the orifices 20, 36 which are defined by the second inner surface portions 28, 46, respectively. Additionally, as best seen in FIG. 7, the thickness of the disc portion 60 is approximately twice the thickness of the connecting arm portions 66, and is substantially equal to the thickness of the flange portion 58 of the ring portion 56.

The valve 10 is preferably assembled in a manner wherein the valve member 54 is initially inserted into the sleeve portion 32 of the first housing half 14. Thereafter, the wall portion 48 of the second housing half 16 is slidably inserted into the sleeve portion 32 in the aforementioned manner. Importantly, when the wall portion 48 is fully inserted into the sleeve portion 32, the flange portion 58 is captured within a first annular channel 70 formed in the base portion 30 of the first housing half 14 and a second annular channel 72 formed in the rim of the wall portion 48. In addition to the flange portion 58 being captured within the channels 70, 72, both the flange portion 58 and ring portion 56 are slightly compressed between the base portion 30 and rim of the wall portion 48. Advantageously, the attachment of the flange portion 50 of the second housing half 16 to the rim of the sleeve portion 32 of the first housing half 14 in the aforementioned manner facilitates the formation of a first seal, with the compression of the ring and flange portions 56, 58 between the first and second housing halves 14, 16 (and in particular the base portion 30 and wall portion 48) facilitating the formation of a second seal. The importance of the first and second seals will be discussed in more detail below.

As seen in FIG. 5, in the valve 10 the valve member 54 is movable between a closed position wherein the disc portion 60 covers and seals the orifice 20, and an open position wherein the disc portion 60 is separated from the orifice 20 and fluid flows from the orifice 20 into the interior chamber 52 and orifice 36 via the side openings 68 of the valve member 54. When the valve member 54 is properly captured between the first and second housing halves 14, 16, the same assumes the orientation shown in FIGS. 5 and 8, and normally resides in the closed position. When in the closed position, the connecting arm portions 66 are flexed slightly toward the second housing half 16, with the inner surface 62 of the disc portion 60 being abutted against the annular shoulder 24 of the first housing half 14, thus covering and sealing the orifice 20. In use, the valve 10 is positioned within a drainage line such that the normal flow of fluid therethrough occurs in the direction shown by the arrow NF. Importantly, when a slight fluid pressure is applied to the inner surface 62 of the disc portion 60 by fluid flowing through the orifice 20 in the direction NF, the disc portion 60 is lifted off of and moves away from the shoulder 24, thus allowing fluid to flow from the orifice 20 into the interior chamber 52 and hence the orifice 36 via the side openings 68. If the valve 10 is subjected to back pressure or a back flow as shown by the arrow BF, such back pressure acts against the outer surface 64 of the disc portion 60, thus causing the inner surface 62 thereof to seat firmly against the shoulder 24 which prevents any back flow into the orifice 20.

Due to the connecting arm portions 66 extending between the ring and disc portions 56, 60 being spirally shaped, the movement of the disc portion 60 away from the shoulder 24 when fluid impinges the inner surface 62 thereof occurs solely as a result of the flexion of the connecting arm portions 66. The movement of the disc portion 60 away from the shoulder 24 solely as a result of the flexing of the connecting arm portions 66 (and not the stretching or elongation thereof) allows the valve member 54 to be moved from the closed to the open positions at very low pressures. The spirally shaped connecting arm portions 66 also allow the disc portion 60 to be separated from the shoulder 24 by a relatively large distance when the valve member 54 is moved to the open position, thus increasing the combined cross-sectional area of the side openings 68 and providing a large fluid flow path between the orifice 20 and interior chamber 52. The combined cross-sectional area of the side openings 68 exceeds the cross-sectional area of each of the second regions of the orifices 20, 36 even when the valve member 54 is in the closed position, with such area being further increased when the valve member 54 is moved to the open position. In view of the combined cross-sectional area of the side openings 68 substantially exceeding the cross-sectional area of each of the second regions of the orifices 20, 36 when the valve member 54 is in the open position, the valve 10 provides extremely low flow resistance or restriction, thus facilitating a high rate of fluid flow through the valve 10 at low pressure and causing a minimal pressure drop between the orifices 20, 36. The symmetrical positioning of the spirally shaped connecting arm portions 66 between the ring and disc portions 56, 60 facilitates the even and flat lifting of the disc portion 60 off of the shoulder 24. Additionally, the resiliency of the connecting arm portions 66 causes the disc portion 60 to quickly return to its sealed engagement with the shoulder 24 when flow in the direction NF is discontinued.

As previously indicated, when the valve member 54 is properly captured between the first and second housing halves 14, 16 and in the closed position, the connecting arm portions 66 are flexed slightly toward the second housing half 16. Such flexion biases the disc portion 60 against the shoulder 24 and causes the opening pressure needed to facilitate the movement of the valve member 54 from the closed to the open positions to be slightly increased. In the valve 10, the valve opening pressure can be further increased by increasing the distance separating the shoulder 24 from the base portion 30 of the first housing half 14 (which will facilitate further flexion of the connecting arm portions 66). Such opening pressure may alternatively be increased by increasing the hardness of the elastomeric material used to fabricate the valve member 54, thereby increasing the stiffness of the connecting arm portions 66.

Since the connecting arm portions 66 are spirally shaped, they have a tendency to cause a slight twisting of the disc portion 60 when the valve member 54 is in the closed position. This twisting could cause distortion of the disc portion 60, and result in retrograde leakage due to the inner surface 62 of the disc portion 60 not being firmly seated (i.e., abutted and sealed) against the shoulder 24. Accordingly, the thickness of the disc portion 60 is increased to approximately twice the thickness of the connecting arm portions 66. Such increased thickness maintains the disc portion 60 in a substantially flat configuration and in sealed engagement with the shoulder 24 when the valve member 54 is in the closed position and a back pressure in the direction BF is exerted against the outer surface 64 of the disc portion 60. As an alternative to increasing the thickness of the disc portion 60, the same can be fabricated from a rigid or semi-rigid material, with the remainder of the valve member 54 being fabricated from the elastomeric material. The fabrication of only the disc portion 60 from the rigid or semi-rigid material can be accomplished by either insert-molding the disc portion 60 or attaching a separate, rigid disc to a molded elastomeric frame. However, integrally molding the disc portion 60 to have twice the thickness of the connecting arm portions 66 is the preferred method of forming the valve member 54 to prevent the distortion of the disc portion 60.

As previously explained, the ring and flange portions 56, 58 of the valve member 54 are compressed and thus trapped like an O-ring between the first and second housing halves 14, 16. Such compression facilitates the formation of the second seal, with the first seal being formed by the ultrasonic joining of the first and second housing halves 14, 16 to each other (i.e., the joining of the flange portion 50 of the second housing half 16 to the rim of the sleeve portion 32 of the first housing half 14). Due to the inclusion of the dual seals in the valve 10, leakage therefrom is prevented when fluid flows therethrough even if the ultrasonic joining of the first and second housing halves 14, 16 to each other is flawed.

Occasionally, when the pressure of an initial flow of fluid in the direction NF is high, the sudden exertion of pressure against the inner surface 62 of the disc portion 60 will facilitate the stretching of the connecting arm portions 66 rather than solely the flexion thereof. As will be recognized, such stretching of the connecting arm portions 66 causes the disc portion 60 to travel significantly further from the shoulder 24 than it normally does when the valve member 54 assumes the open position. In this respect, if the pressure exerted against the inner surface 62 of the disc portion 60 is great enough, the same may be forced through a substantial portion of the interior chamber 52 and against the inner surface 40 of the second housing half 16. To prevent the disc portion 60 from sealing against the inner surface 40 and blocking fluid flow into the orifice 36, the bosses 41 are formed on the inner surface 40. As will be recognized, the abutment of the outer surface 64 of the disc portion 60 against the bosses 41 rather than the inner surface 40 prevents the disc portion 60 from sealing against the inner surface 40 and allows fluid to flow between the disc portion 60 and bosses 41 into the orifice 36. When the pressure of the flow in the direction NF returns to a normal, low pressure level, the disc portion 60 will return to its usual open position.

Referring now to FIG. 9, the valve 10 may alternatively be provided with a second housing half 16a which is identical to the second housing half 16 previously described, but does not include the bosses 41 formed on the inner surface 40a thereof. As will be recognized, when the valve 10 is constructed to include the second housing half 16a, a high pressure surge against the inner surface 62 of the disc portion 60 will cause the same, and in particular the peripheral edge of the outer surface 64 thereof, to seal against the inner surface 40a. In non-medical applications, the sealing of the disc portion 60 against the inner surface 40a acts as a surge protector which prevents a sudden high pressure flow of fluid through the valve 10. However, in medical applications, the valve 10 incorporating the second housing half 16 including the bosses 41 will be utilized since it is extremely important that the flow of fluid through the valve 10 never be blocked.

Figure 10B:
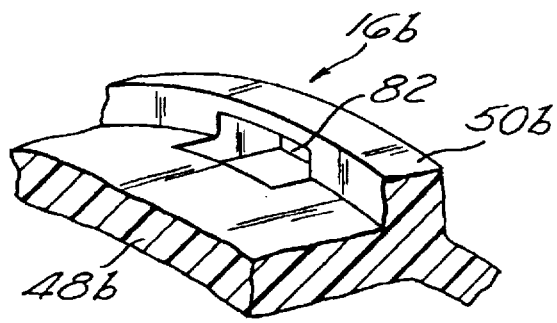
FIG. 10b is a partial perspective view of a second half of the housing of the valve which is constructed in accordance with a third embodiment of the present invention.
Figure 10C:
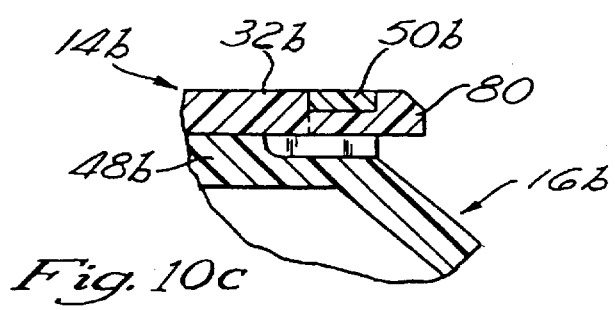
FIG. 10c is a partial cross-sectional view of the first and second housing halves shown in FIGS. 10a and 10b as attached to each other.

Referring now to FIGS. 10a, 10b, and 10c, the valve 10 may also comprise first and second housing halves 14b, 16b. The first housing half 14b is identical to the first housing half 14 previously described, but further includes a hook shaped latch portion 80 extending outwardly from the rim of the sleeve portion 32b thereof. The second housing half 16b is identical to the second housing half 16 previously described, bug further includes an arcuately shaped notch 82 disposed within the wall and flange portions 48b, 50b thereof. Rather than being rigidly attached to each other via ultrasonic welding, an adhesive, or solvent, the first and second housing halves 14b, 16b are adapted to be attached to each other via snapping engagement through the receipt of the latch portion 80 into the notch 82.

Figure 11:
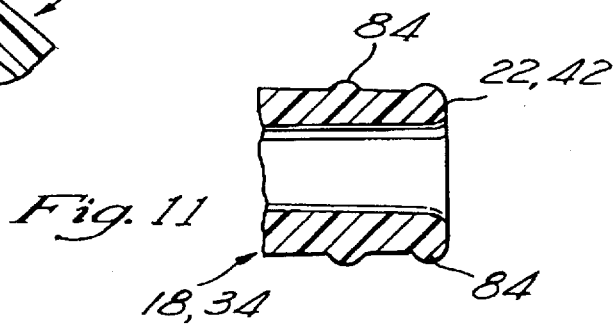
FIG. 11 is a partial cross-sectional view of an adapter portion of a housing half including female Luer threads formed thereon.
Figure 12:
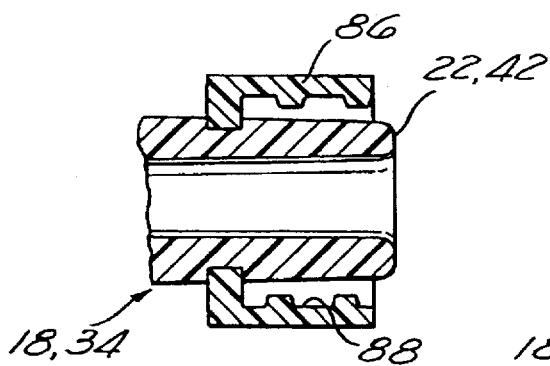
FIG. 12 is a partial cross-sectional view of an adapter portion of a housing half including a connector member rotatably connected thereto.
Figure 13:
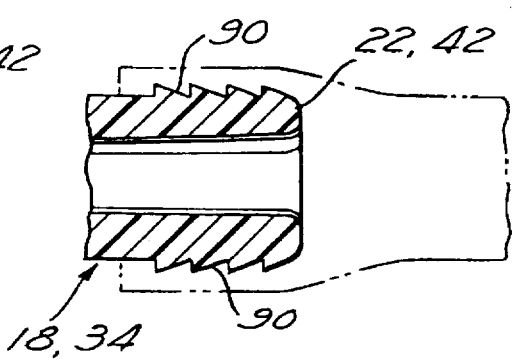
FIG. 13 is a partial cross-sectional view of an adapter portion of a housing half including barbs formed thereon.

Referring now to FIG. 11, one or both of the adapter portions 18, 34 of the first and second housing halves 14, 16 may include female Luer threads 84 formed thereon adjacent the outer ends 22, 42 thereof. Additionally, as seen in FIG. 12, one or both of the adapter portions 18, 34 may include a connector cap 86 rotatably connected thereto which defines threads 88 within the inner surface thereof. Moreover, as seen in FIG. 13, one or both of the adapter portions 18, 34 may include barbs 90 formed thereon adjacent the outer ends 22, 42 thereof. It will be recognized that the male Luer threads 84, connector cap 86, or barbs 90 may be included on the adapter portions of the first housing half 14b and second housing halves 16a, 16b as well.

The valve 10 constructed in accordance with the present invention is typically used in a variety of medical applications. As seen in FIG. 1, such applications include the incorporation of the valve 10 into a urine drainage line 74 from a Foley or suprapubic catheter into a collection bag 76. As seen in FIG. 2, the valve 10, due to its low flow resistance, may also be used to allow patients with a tracheotomy to talk, and may thus serve as a replacement for the widely utilized Passey-Muir Trach valve. The valve 10 may also be used in relation to the drainage of blood from a post-operative site such as the chest, knee or hip, or in relation to the intravenous administration of fluids. When used in intravenous applications, the valve 10 may be provided with Luer fittings at one or both ends of the housing 12. The valve 10 may further be utilized in respiratory or patient ventilatory circuits. Due to its extremely low flow resistance, the valve 10 is usable in such circuits since it will open and close in response to a patient's breathing efforts. Finally, the valve 10 may be used in medical fluid pumping applications such as with a Cornwall syringe used in hospital pharmacies for fluid admixtures, and in medical diagnostic instrumentation requiring unidirectional fluid flow. In addition to the previously described medical applications, the valve 10 (including either the second housing half 16 or 16a) may be used in other applications such as automotive, chemical and laboratory applications which require reliable, one-way check valves with low opening pressure and low flow resistance. Due to its construction, the valve 10 is orientation independent, and need not be maintained in a particular horizontal or vertical orientation to function properly.

Though as shown in FIG. 1, the valve 10 is typically incorporated into a fluid line via the connection of separate segments of the fluid line to respective ones of the adapter portions 18, 34, it will be recognized that the valve 10 may also be positioned directly within the lumen of a fluid line or the bore of a fluid conduit. In this respect, for applications wherein the valve 10 is to be positioned within the lumen/bore, the housing 12 may be formed so as not to include the tubular adapter portions 18, 34.

Additional modifications and improvements of the present invention may also be apparent to those skilled in the art. Thus, the particular combination of parts described and illustrated herein is intended to represent only certain embodiments of the present invention, and is not intended to serve as limitations of alternative devices within the spirit and scope of the invention.

What is claimed is:

1. A low actuation pressure, unidirectional flow valve comprising:
    a housing including a fluid flow passage extending therethrough which defines first and second sections; and
    a valve member disposed within said housing between said first and second sections of said flow passage, said valve member comprising:
        an annular ring portion;
        a disc portion disposed within said ring portion;
        at least two connecting arm portions extending between said ring and disc portions in symmetrical relation to each other; and at least two side openings defined by said ring, disc and connecting arm portions;

said valve member being movable between a closed position wherein said disc portion covers and seals the first section of the flow passage and an open position wherein said disc portion is separated from said first section and fluid flows from said first section to said second section via said side openings, the movement of the valve member between the closed and open positions being facilitated by the flexion of the connecting arm portions;

said valve member being configured such that when in the open position, the combined cross-sectional area of the side openings exceeds the minimum cross-sectional area of the first section of the flow passage.

2. The valve of claim 1 wherein each of said connecting arm portions is spirally shaped.

3. The valve of claim 2 wherein each of said side openings has a serpentine configuration.

4. The valve of claim 2 wherein said valve member includes four (4) connecting arm portions symmetrically positioned between the ring and disc portions, and four (4) side openings defined by the ring, disc and connecting arm portions.

5. The valve of claim 1 wherein the thickness of the disc portion exceeds the thickness of the connecting arm portions.

6. The valve of claim 5 wherein the thickness of the disc portion is approximately twice the thickness of the connecting arm portions.

7. The valve of claim 1 wherein said disc portion is fabricated from a rigid material and said ring and connecting arm portions are fabricated from an elastomeric material.

8. The valve of claim 1 wherein said disc portion is fabricated from a semi-rigid material and said ring and connecting arm portions are fabricated from an elastomeric material.

9. The valve of claim 1 wherein said housing comprises:

a first housing half defining the first section of the flow passage; and a second housing half defining the second section of the flow passage, said second housing half being partially inserted into and rigidly attached to said first housing half;

said ring portion being compressed and rigidly captured between the first And second housing halves, with the attachment of the first and second housing halves to each other facilitating the formation of a first seal and the compression of the ring portion between the first and second housing halves facilitating the formation of a second seal.

10. The valve of claim 9 wherein said first housing half includes an inner, annular shoulder which defines one end of the first section of the flow passage, said disc portion being abutted and sealed against said shoulder when the valve member is in the closed position and separated from said shoulder when the valve member is in the open position.

11. The valve of claim 9 wherein the second housing half includes a plurality of bosses formed therewithin for preventing the disc portion from sealing against the second housing half when the valve member is moved to the open position under high pressure.

12. The valve of claim 9 wherein said first and second housing halves are each fabricated from a plastic material.

13. The valve of claim 12 wherein said first and second housing halves are each fabricated from a transparent plastic material.

14. The valve of claim 9 wherein said first and second housing halves are attached to each other via an ultrasonic welding process.

15. The valve of claim 9 wherein said first and second housing halves are attached to each other via an adhesive.

16. The valve of claim 9 wherein said first and second housing halves are attached to each other via a solvent.

17. The valve of claim 9 wherein said first housing half includes a latch portion formed thereon and said second housing half includes a notch formed therein, said first and second housing halves being attached to each other via snapping engagement through the receipt of the latch portion into the notch.

18. The valve of claim 9 wherein said first and second housing halves each include an adapter portion having female Luer locking threads formed thereon.

19. The valve of claim 9 wherein said first and second housing halves each include an adapter portion having a male Luer taper and a connector member rotatably connected thereto.

20. The valve of claim 9 wherein said first and second housing halves each include an adapter portion having barbs formed thereon.

21. The valve of claim 9 wherein said second housing half further defines a frusto conical inner surface portion, said disc portion sealing against said inner surface portion to provide surge protection in the event the valve is subjected to a sudden high pressure flow of fluid therethrough.

22. The valve of claim 1 wherein said housing is sized and configured to be positionable within a lumen of a fluid line.

23. The valve of claim 1 wherein the valve member is fabricated from an elastomeric material.

* * * * *